(12) United States Patent  
Annis

(10) Patent No.: US 6,702,167 B2
(45) Date of Patent: Mar. 9, 2004

(54) BREASTPUMP BACKPACK

(75) Inventor: Larry D. Annis, Elgin, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 09/860,813

(22) Filed: May 18, 2001

(65) Prior Publication Data

US 2002/0170935 A1 Nov. 21, 2002

(51) Int. Cl.$^7$ ............................................... A45C 15/00
(52) U.S. Cl. ..................... 224/576; 224/652; 224/653; 224/657; 604/35; 604/74; 604/120; 604/121
(58) Field of Search ................. 224/576, 652, 224/653, 657, 680, 681, 682, 684; 604/73, 74, 75, 76, 30, 31, 35–38, 118, 119, 120, 121

(56) References Cited

U.S. PATENT DOCUMENTS

| | | | |
|---|---|---|---|
| 4,607,596 A | | 8/1986 | Whittlestone et al. ... 119/14.02 |
| 4,706,856 A | * | 11/1987 | Jacober ........................ 224/153 |
| 4,710,165 A | | 12/1987 | McNeil et al. ................. 604/67 |
| 4,772,262 A | | 9/1988 | Grant et al. ................... 604/74 |
| 4,941,603 A | * | 7/1990 | Creamer et al. ............. 150/109 |
| 5,004,134 A | * | 4/1991 | Barry .......................... 224/235 |
| 5,090,526 A | * | 2/1992 | Jacober ........................ 190/107 |
| 5,337,934 A | * | 8/1994 | Johnson et al. ........... 224/148.5 |
| 5,571,084 A | * | 11/1996 | Palmer .......................... 601/14 |
| 5,616,125 A | * | 4/1997 | Jelks ............................ 601/14 |
| 5,776,098 A | * | 7/1998 | Silver et al. ................... 604/74 |
| 5,873,504 A | * | 2/1999 | Farmer ....................... 150/113 |
| 6,015,072 A | * | 1/2000 | Young ......................... 190/103 |
| 6,139,521 A | * | 10/2000 | Larsson ....................... 604/315 |
| 6,238,091 B1 | * | 5/2001 | Mogil .......................... 383/110 |
| 6,257,847 B1 | | 7/2001 | Silver et al. ................. 417/415 |
| D457,307 S | * | 5/2002 | Pukall et al. ................. D3/216 |

* cited by examiner

Primary Examiner—Stephen K. Cronin
(74) Attorney, Agent, or Firm—Baniak Pine & Gannon

(57) ABSTRACT

A breastpump carrier in the form of a backpack. The breastpump backpack has a horizontal shelf dividing the interior of the breastpump carrier into lower and upper storage areas. The lower storage area is accessible through an exterior side of the backpack with a pumping mechanism mounted therein.

11 Claims, 7 Drawing Sheets

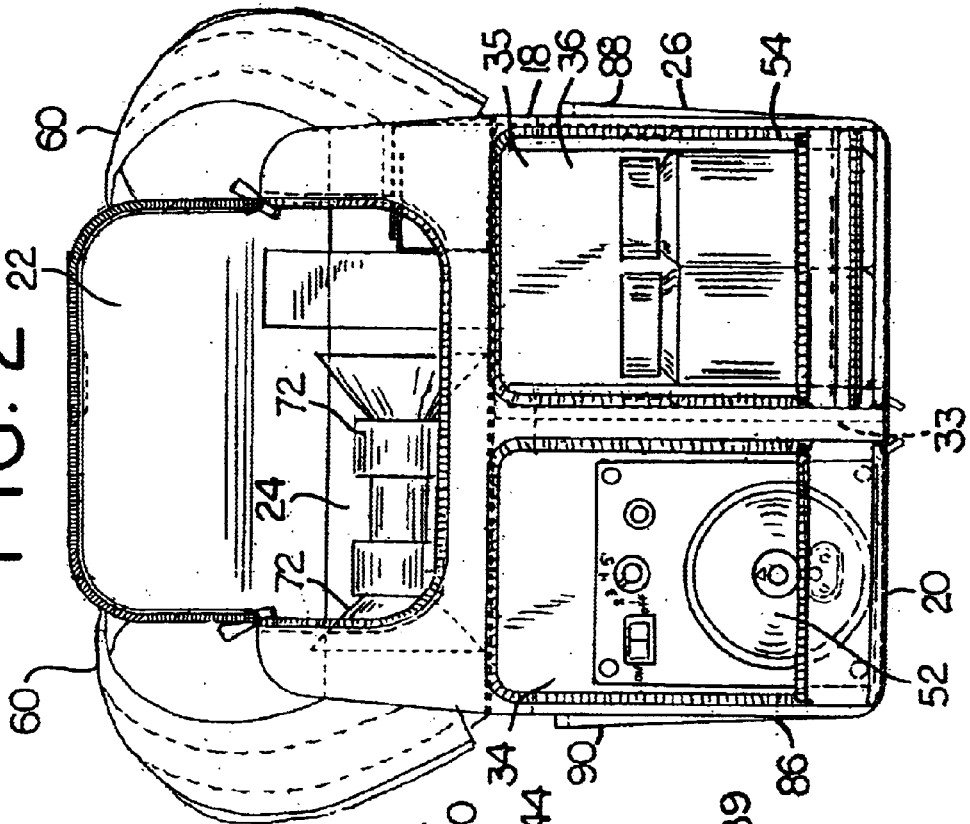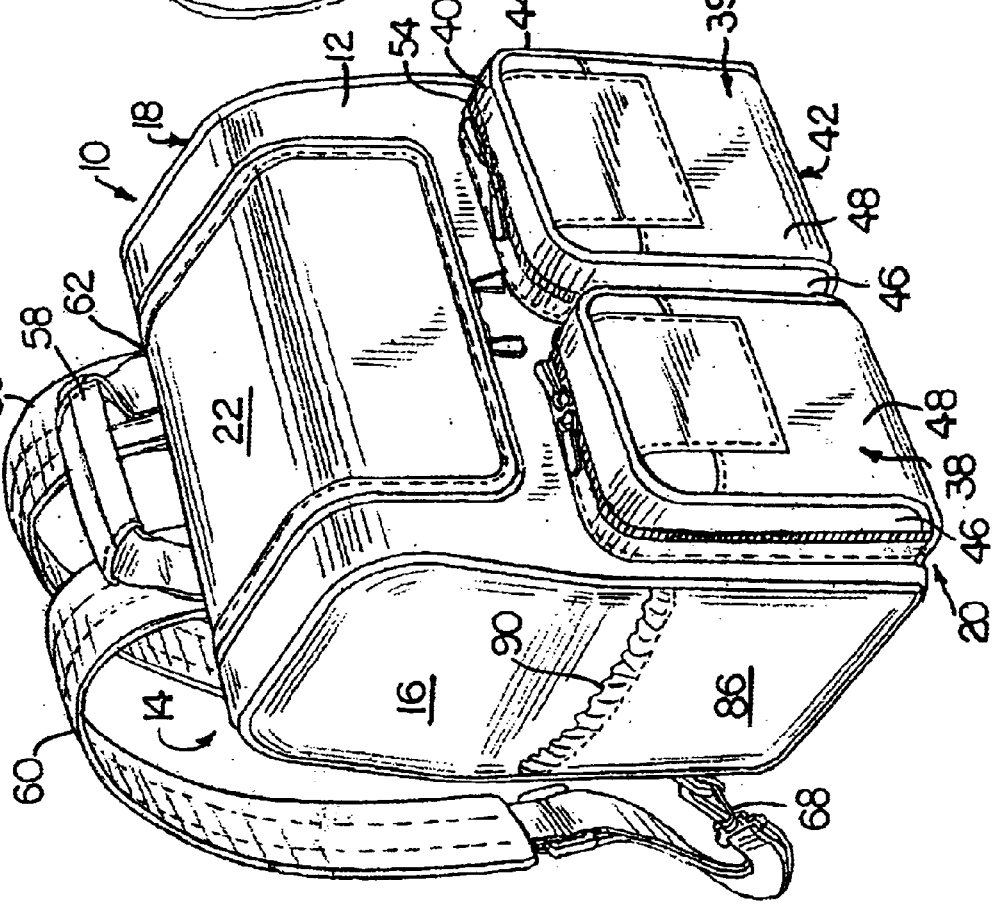

BREASTPUMP BACKPACK

FIELD OF THE INVENTION

The invention relates to breastpumps, and more particularly to a carrier for a breastpump.

DESCRIPTION OF THE PRIOR ART

Breastpumps are convenient for nursing mothers, such as for working mothers, because they allow nursing mothers to pump breast milk when the child is unavailable to feed. The expressed milk may furthermore be saved to feed to a child at a later time, when the mother may not be present. For some mothers, breastpumps are necessary when the child has suckling difficulties, or if the mother has problems with excessive, or alternatively deficient, milk production. Some mothers also require breastpumps in the event of soreness or injury of the breast.

Motor-driven pumps for breastpumps, such as battery-powered (D.C.) or conventional house-current powered (A.C.), have been marketed. The pumps are often made for operating two breastshield assemblies at once, i.e., providing for "double pumping."

Carrying cases for motor-drive breastpumps have been developed. They generally comprise a rigid case from which the motor drive is removed for use.

A recent innovation is U.S. Pat. No. 5,776,098 (incorporated herein by reference), which describes a lightweight diaphragm-type motor-driven breastpump. The pumping mechanism is mounted within a support frame contained within a soft carrying case. The face of the breastpump has spigots for attaching tubing that connects to breastshield assemblies. It also has controls which regulate the vacuum and allow the pump to be turned on and off, that are accessible from the outside of the carrying case.

The carrying case described in U.S. Pat. No. 5,776,098 was commercialized as the Pump In Style breastpump. It furthermore has a number of compartments for storing such items as the breastshields, tubing, batteries, and a D.C. converter for use with an A.C. power supply. This carrying case allows for convenient transportation of the breastpump. The present invention builds upon the success of the foregoing Pump In Style®) carrying case, and represents another innovative device for carrying a breastpump and related equipment.

SUMMARY OF THE INVENTION

It is a principal objective of the invention to provide a breastpump carrier comprising a backpack. In one preferred embodiment, a horizontal shelf divides the interior of the backpack into a lower storage area and an upper storage area. The upper storage area is dimensioned to hold items such as the breastshields, tubing, a battery, a D.C. converter for use with an A.C. power supply, and the like. A vertical wall may be provided, as in one embodiment, to separate the lower storage area into a pump storage compartment and an insulated storage compartment. An access opening advantageously provides access to the pump storage compartment and the insulated storage compartment from the outside of the backpack.

The pump storage compartment is used for mounting/housing a motorized pump therein. One or two spigots are presented that are accessible from the outside for attaching tubing to one or two breastshields. The insulated storage compartment is lined with an insulating material, and is most advantageously used for storage of a plurality of baby bottles and a cooling means, such as an ice (e.g., gel) pack.

In a preferred form, at least one securable/sealable cover provides a closure for the access opening to the upper storage area, i.e., the top of the backpack. The backpack can have separate sealable covers for the pump storage compartment and the insulated storage compartment. Additionally, one or more pockets can be located on the sealable covers, the sides of the backpack, or elsewhere on the backpack.

One or two straps are attached to the exterior of the backpack. The straps have an upper shoulder engaging portion and a lower bottom portion, and are attached on the back of the breastpump carrier. The back straps are preferably adjustable. The backpack additionally can have a carrying handle mounted on the top of the breastpump carrier, for hand carrying.

In another form of the invention, the backpack has a single sealable cover to provide closure of the compartment(s) in the storage area. In addition, a separate sealable cover for the insulated storage compartment is located within the single sealable cover.

In yet another aspect of the invention, the horizontal shelf can be collapsed against the interior of the backpack, the vertical wall (where provided) can be collapsed, and the lining of the insulated storage compartment can be collapsed, to thereby form a single large storage area. The breastpump motor drive is removably mounted so that it can be taken out of its compartment. These collapsible features of the breastpump carrier then allow for general use of the backpack when it is not being used to specifically carry a breastpump.

In yet another form of the invention, the horizontal shelf and any other interior structure are connected in a detachable manner to the interior (sides, bottom, front, and/or back) of the backpack. These can then be temporarily removed from the interior of the breastpump carrier to form the large storage area.

In still another form of the invention, a pump container has the motor (and related pumping mechanism) therein, and is constructed to fit within a compartment in the lower portion of the interior of the breastpump carrier. The pump container allows for convenient removable mounting of the pump elements, providing a user direct access to the pump and controls, such as from the outside of the backpack, and easy removal of the same for the aforementioned use of the backpack alone.

Additionally, an insulated container is constructed to fit through the closable top of the backpack in the upper storage area. In the foregoing form of the invention, it rests on the horizontal shelf. The insulated container is primarily used for storage of a plurality of baby bottles and a cooling means, such as a coolant pack(s). The insulated container advantageously has a strap or handle for easy removal and handling. Remaining space in the top interior portion of the breastpump carrier may be used for storage of one or two breastshields, tubing, batteries, and infant needs, such as diapers, wipes, tissues, lotions, and medications.

These and other advantages of the present invention will be further understood and appreciated upon consideration of the following detailed description of embodiments of the invention taken in conjunction with the drawings, in which:

BRIEF DESCRIPTION OF THE DRAWINGS

FIG. 1 is a perspective front elevational view of a first embodiment of a breastpump backpack made in accordance with the invention;

FIG. 2 is a front elevational view with access flaps open showing the interior of the breastpump backpack of FIG. 1;

Unless otherwise specified, in the drawings, like parts have like numbers.

DETAILED DESCRIPTION OF PREFERRED EMBODIMENTS

Figure 4:
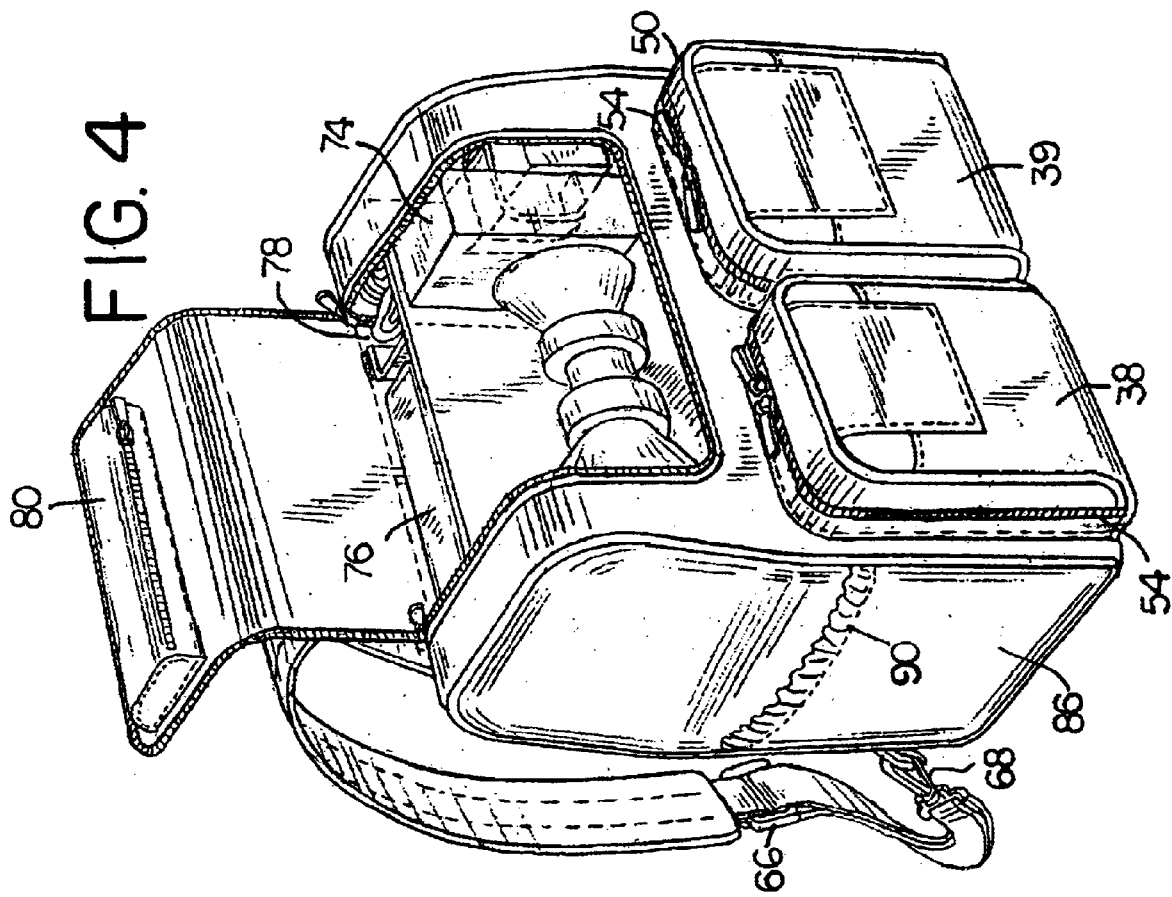
FIG. 4 is a perspective front elevational view of the breastpump backpack of FIG. 1, with the top flap open.
Figure 3:
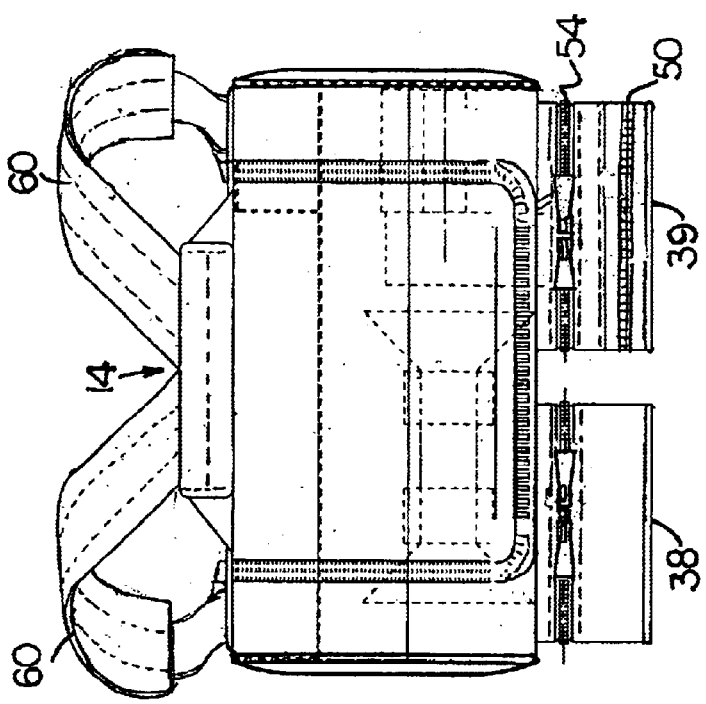
FIG. 3 is a top view of the breastpump backpack of FIG. 1.

A breastpump carrier of the present invention is shown in a first embodiment as a breastpump backpack of FIGS. 1 through 6. Referring first to FIGS. 1 and 2, the backpack 10 has a front 12, a back 14, sides 16 and 18, a bottom 20. A closeable top 22 provides access to the interior 24 of the backpack through the top.

The interior 24 is divided by a horizontal shelf 28, which is perhaps shown best in FIG. 4, into a lower area 30 and an upper area 32. A vertical wall 33 (FIG. 2) divides the lower storage area 30 into a pump mechanism storage compartment 34 and an insulated storage compartment 36.

The backpack 10 has one or more covers 38 and 39. The covers 38, 39 each have a top 40, a bottom 42, sides 44 and 46, and front 48. The sealable cover 38 allows access to the front of motorized pump 52. Cover 39 provides access to the insulated storage compartment 36. Details of the pump 52 and its mounting within a compartment 36 of this type can be gleaned from U.S. Pat. No. 5,776,098.

The sealable covers 38, 39 are closed by means of zippers 54, although other closures can be used. Insulated storage compartment 36 actually has a two-piece cover 39, which yields a front pocket accessed by zipper 50 (FIGS. 3 and 5), and the more inboard zipper 54 that opens the compartment 36.

Figure 6:
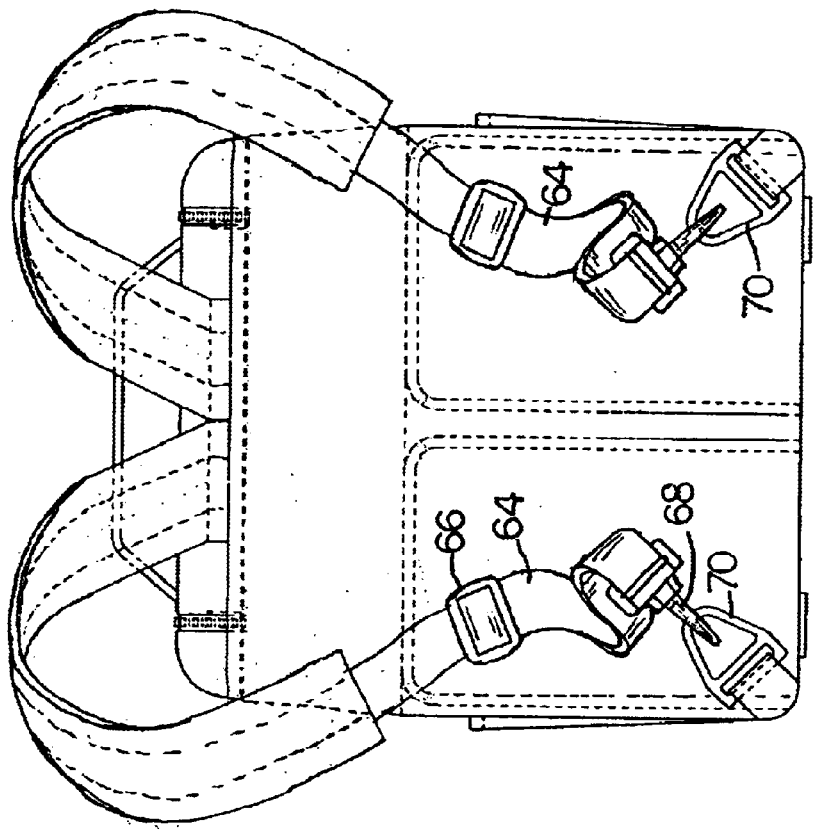
FIG. 6 is an elevational rear view of the breastpump backpack of FIG. 1.
Figure 5:
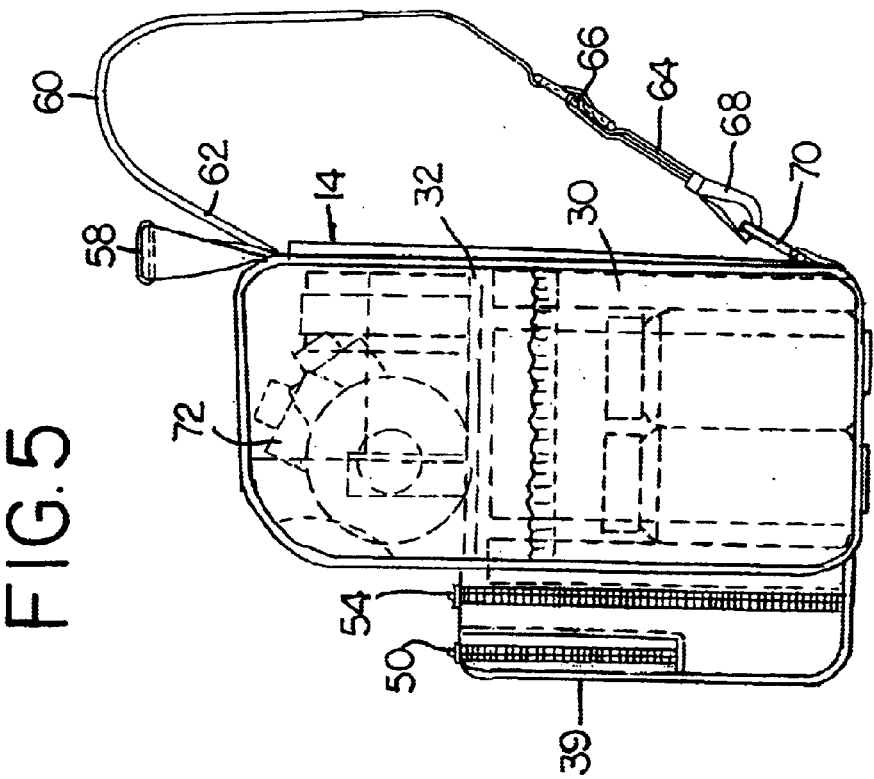
FIG. 5 is an elevational side view of the breastpump backpack of FIG. 1.

The breastpump backpack has a handle 58, which is shown as being a single loop handle mounted to the rear of top 22. Two back straps 60 are mounted on the exterior back 14 of the breastpump carrier 10. The back straps 60 have an upper portion 62 and a lower portion 64 (FIG. 6). The upper portion 62 of each back straps 60 is fitted to the back 14 near the top 22. The lower portion 64 of back straps 60 is adjustable by means of a buckle 66. The ends of lower portion 64 of each back strap contain a clip 68, which is shown for example in FIGS. 5 and 6. Each clip 68 is adapted to engage a ring 70. Ring 70 is attached to the back 14 of the breastpump carrier 10 near the bottom and side.

The upper storage area 32, as shown in FIGS. 2 and 4, is dimensioned so that breastshields 72 and a D.C. converter 74 (for use with an A.C. power supply) can be stored within. Empty bottles may also be stored in upper storage area 32. In this embodiment, upper storage area 32 contains rearwardly positioned storage compartments 76 and 78. Compartment 76 may contain instruction manuals and miscellaneous items, for instance, whereas compartment 78 is suited for the storage of the tubing used to connect the breastshields 72 to the motorized pump 52. In one form of the preferred embodiment, the interior of closeable top 22 is fitted with a battery-carrying sleeve 80 (FIG. 4).

It is also desirable to provide the breastpump backpack 10 with one or more side pockets 86 and 88, which are shown in FIG. 1 for instance, having an elasticized strip 90 to function as a closure.

Figure 7:
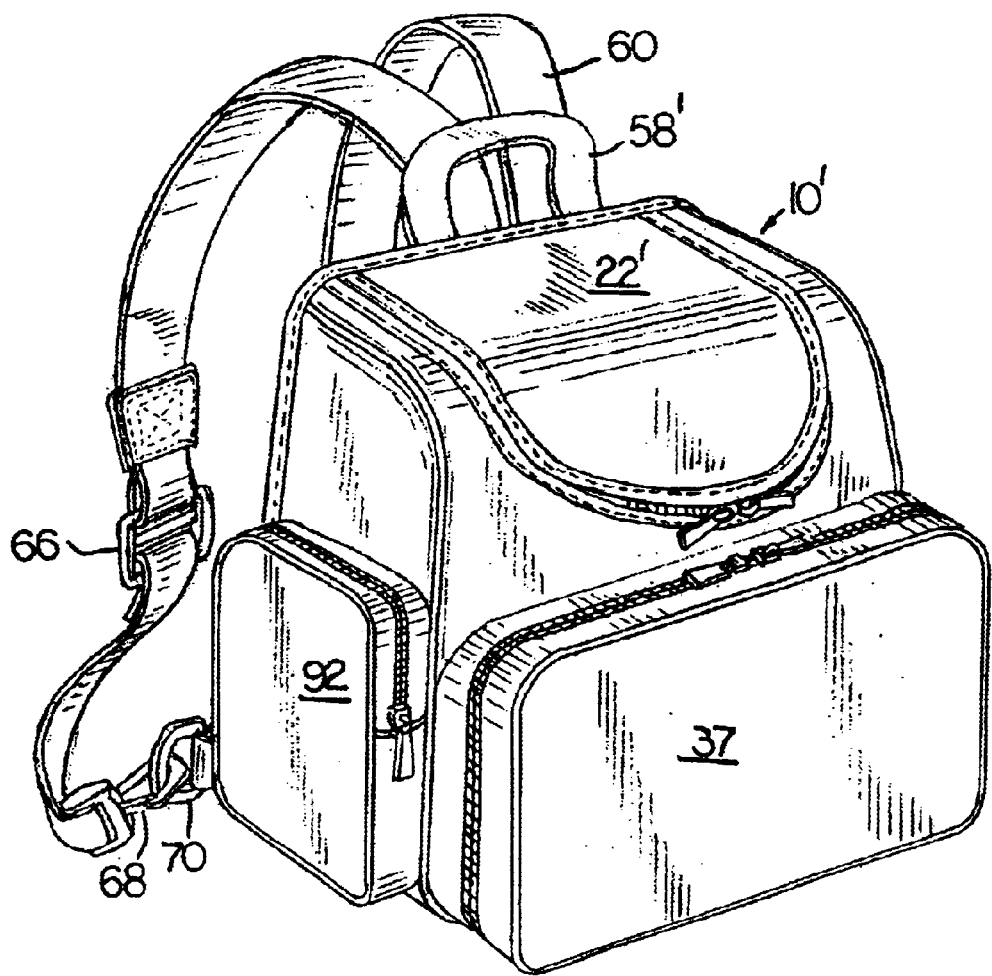
FIG. 7 is an elevational perspective view of a breastpump backpack in another embodiment, showing a single sealable cover and a side pocket.

FIG. 7 shows a modified version of the backpack breastpump, here indicated at 10' (prime numbers being substantially similar to their unprimed counterparts). A single front cover 37 is provided over the compartments for the pump and cold storage (not shown, but the same as previously described with respect to FIGS. 1 through 6). A side zippered compartment 92 replaces pocket 86. Top cover flap 22' has a more curved perimeter. Handle 58' is slightly modified from its counterpart in the embodiment of FIGS. 1 though 6.

A neat compact breastpump backpack is thus provided by the invention. It may be carried using the carrying handle 58' or on one's back using the straps 60. If it is desirable to transport the breastpump carrier 10 on a single shoulder, clip 68 may be disengaged from rings 70, and attached to each other, thus converting the back straps 60 into a sling-type carrier, or a single strap can be employed.

Turning to another aspect, the insulated storage compartment 36 has a lining (FIG. 2) of pliable insulative material that is connected to the interior front 12 of the storage compartment 36. The horizontal shelf 28 is capable of being lifted for access to the open top of compartment 34, for access to the pump compartment (as for installation or removal of the pump 52). This is accomplished via a hinge connection of the horizontal shelf 28 at the interior back wall, and a releasable hook and loop fastening between the shelf and the interior front wall.

The vertical wall 33 and the lining 37 of the insulated storage compartment 36 can likewise be connected in a detachable/foldable manner to the interior of the breastpump carrier to form a large storage area in the event that the motor 52 is removed from compartment 36.

The invention thus further provides for conversion to a simple backpack for use without the breastpumping equipment mounted therein, i.e., as a backpack per se.

Figure 8:
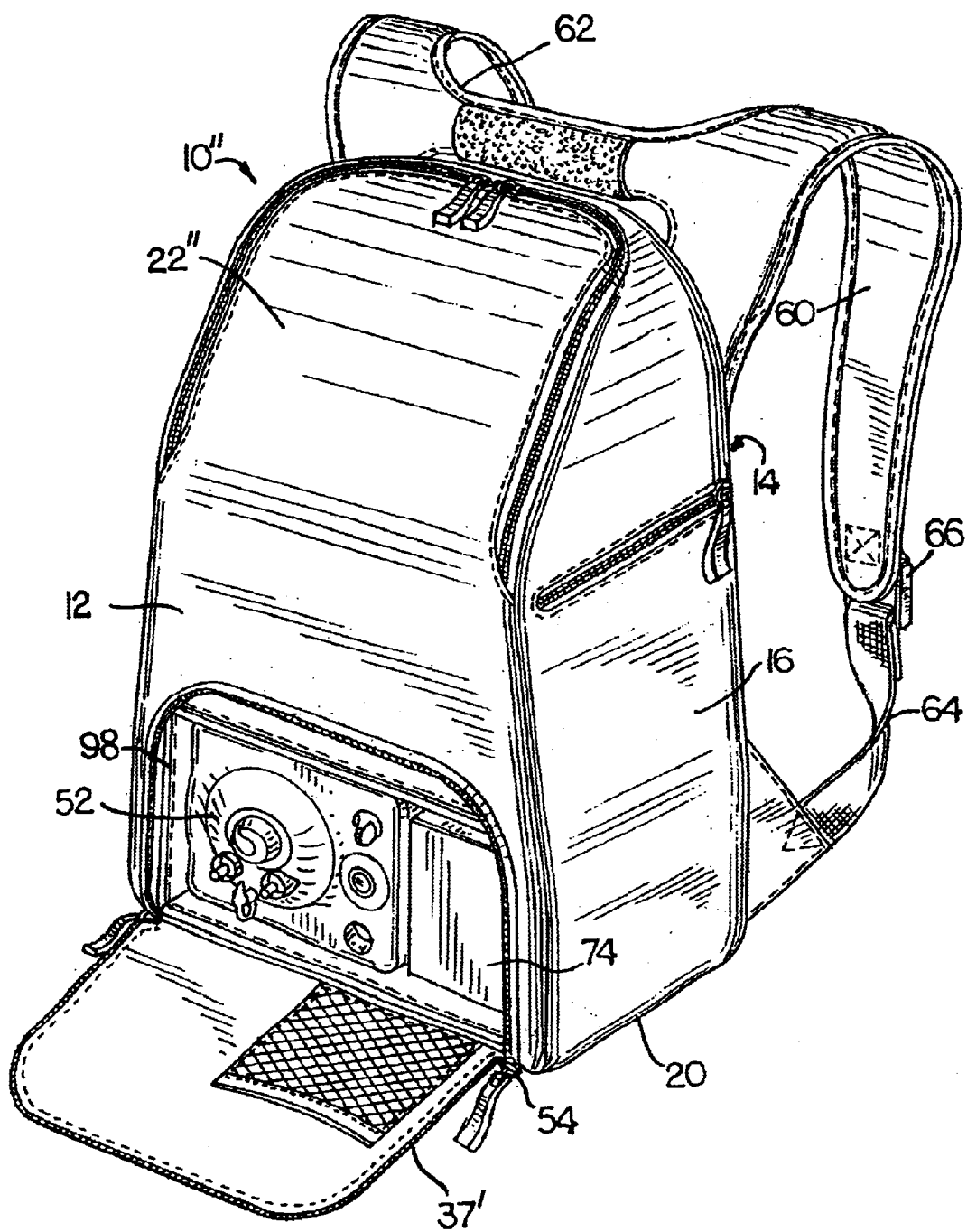
FIG. 8 is a perspective front elevational view of yet another embodiment of the breastpump backpack.
Figure 9:
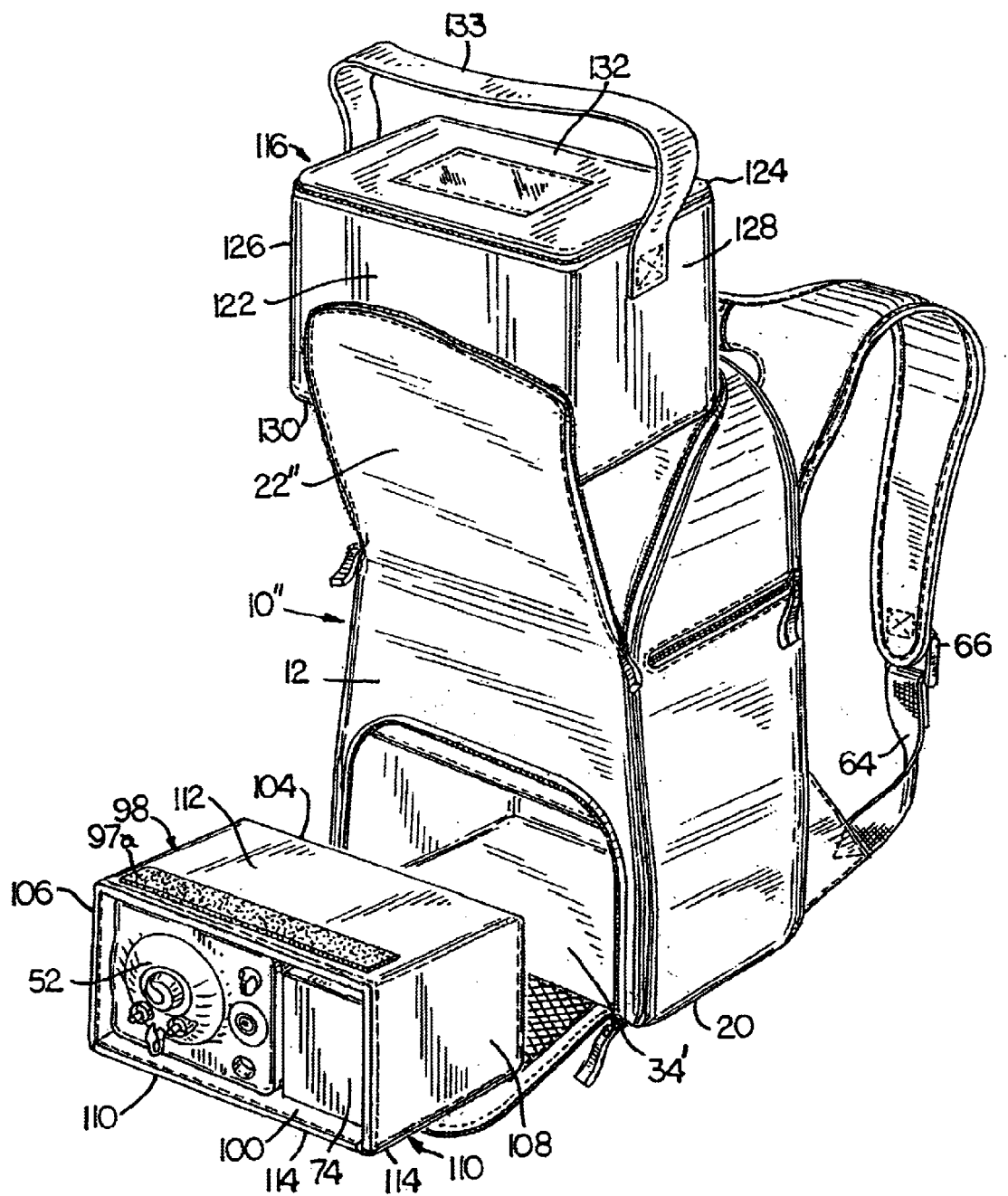
FIG. 9 is a perspective front elevational view of the breastpump backpack of FIG. 8 showing the interior positioning of an insulated container and pump container.
Figure 10:
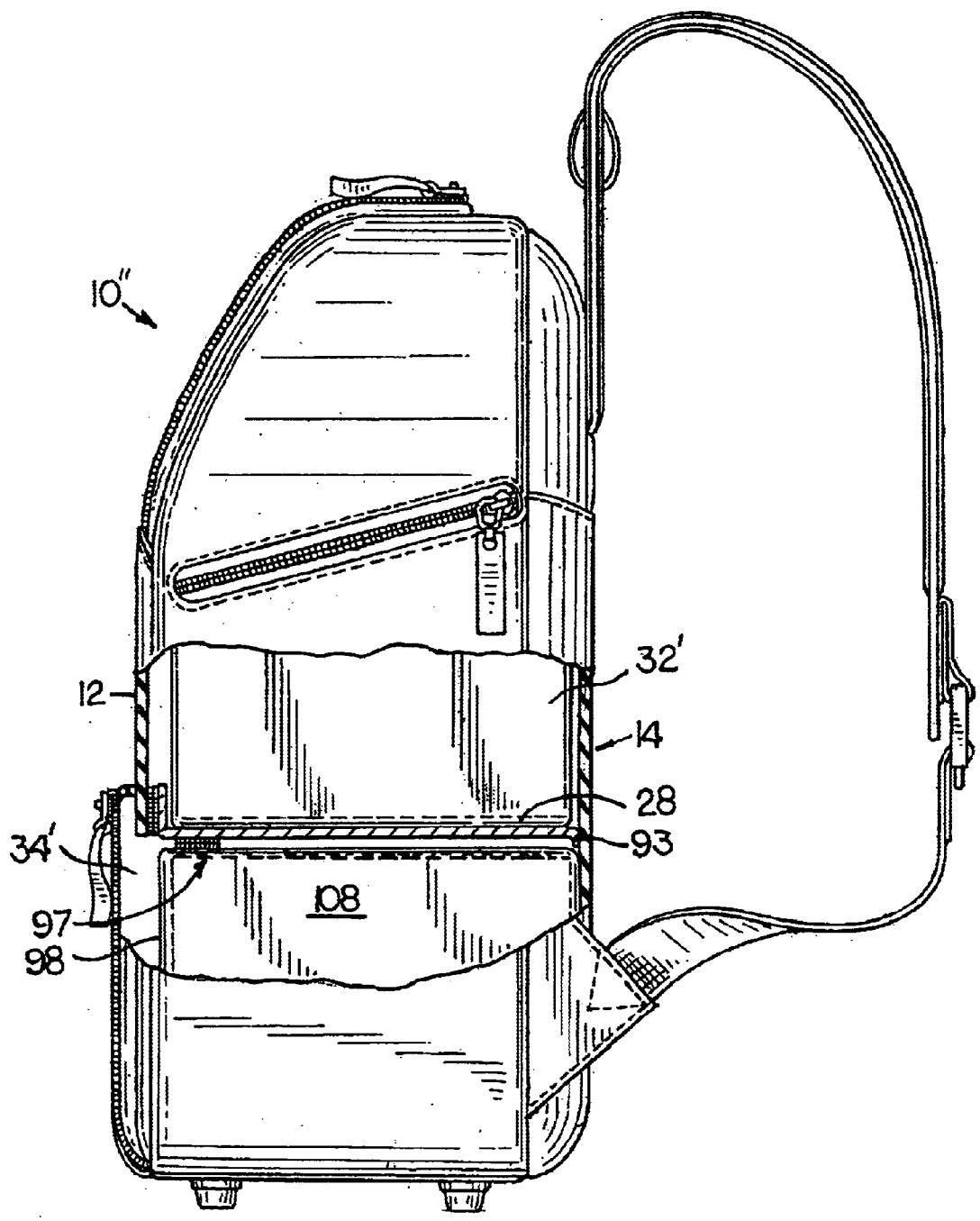
FIG. 10 is a side elevation view of the breastpump backpack of FIG. 9, partially broken-away to show interior structure.

This form of the invention is best illustrated in the embodiment shown in FIGS. 8, 9, and 10. The horizontal shelf 28 is hingedly connected along the interior side of the back 14 (as by stitching thereto along a fabric hinge at 93 (FIG. 10). Hook-and-loop fastener 95 releasably attaches the upturned front 28a of the shelf 28 to the interior wall of the front 12.

A pump container 98 has an interior 100, a back 104, two sides 106 and 108, a bottom 110, and a top 112. A closable front flap 114 is hinged (by a fabric hinge) at the bottom 110 front edge; in FIG. 9, it is shown folded in facial engagement with the bottom 110, which would be its position for insertion in pump compartment 34'. The breastpump container 98 is used for storage of a pump 52 and a D.C. converter 74 for use with an A.C. power supply. The breastpump container 98 is constructed of rigid material for the six walls, covered by soft fabric. Container 98 fits snugly within compartment 34', and slides easily in and out. When removed, the closeable front 114 is secured to close the container 98 by a hook and loop fastener, half of which is shown at 97a; the other complementary half is shown in FIG. 10.

An insulated container 116 having a front 122, a back 124, two sides 126 and 128, a bottom 130, and a closeable top 132 is likewise constructed to snugly fit through the closable top 22" to fill the upper area 32' of the interior of the breastpump backpack 10". The closeable top 132 of the insulated container can be secured closed by use of a zipper or other suitable securing means (as is true for all of the various closures herein). The insulated container 116 is primarily used for storage of a plurality of baby bottles and a cooling means, such as an ice pack. Like the pump container 98, the insulated container 116 is constructed of rigid material (for the walls) covered by a soft-sided fabric. A handle-strap 133 is attached to the insulated container 116 for ease in carrying and removal.

The remaining space in the top interior of the breastpump backpack 10" may be used for storage of one or two breastshields 72, or other equipment needed or desired for use with the breastpump 52, or infant needs, such as diapers, wipes, tissues, lotions, and medications. The insulated container 116 sits upon shelf 28 when placed in the backpack 10".

Referring to FIG. 10, hook-and-loop fastener 97 is used to further anchor the horizontal shelf, here to the top of the container 98, while also serving to secure the container 98 within compartment 34'.

It will thus be apparent that conversion of the backpack 10" from a carrier for a pump 52 (and related equipment, e.g., insulated container 116) to a pure backpack, is readily and easily accomplished in this embodiment. The containers 98 and 116 are simply removed, and shelf 28 collapsed against the interior wall of back 14. The entire interior of the backpack is then available for storage. Reversal of the process to carry the pump and related elements is just as easily accomplished.

Although preferred embodiments of the invention have been described in the foregoing description and illustrated in the accompanying drawings, the invention is not intended to be limited to the specific embodiments disclosed, but is capable of numerous changes, rearrangements and modifications without departing from the scope of the invention. Accordingly, the claims hereafter to the present invention are intended to encompass such changes, rearrangements and modifications as fall within the scope of the invention.

What is claimed is:

1. A breastpump carrier, comprising:
   a backpack having an interior, an exterior, a front, a back, sides, a bottom, and a closeable top;
   a horizontal shelf dividing the interior of the breastpump carrier into lower and upper storage areas, said lower storage area being accessible through an access port;
   a motorized pump for generating air pressure to operate a breastpumping device;
   a pump storage compartment located within said interior, which is sized and shaped to receive said pump, said pump storage compartment having a cover which is openable from said backpack exterior to access said pump for use thereof without removing said pump from said storage compartment;
   an insulated storage compartment located within said interior, said insulated storage compartment having a cover which is openable from said backpack exterior;
   at least one strap on said backpack adapted to mount said backpack on the shoulder of a person; and
   said horizontal shelf is collapsible within said backpack, and said motorized pump is removably mounted within said pump storage compartment.

2. The breastpump carrier of claim 1 wherein said upper storage area has a plurality of compartments defined therein.

3. The breastpump carrier of claim 1 wherein said backpack is made of a soft flexible material.

4. A breastpump carrier, comprising a backpack defining a vertical rectangular case having an interior, an exterior, a front, a back, two sides, a bottom, and a closeable top;
   a horizontal shelf dividing the interior of the breastpump carrier into lower and upper storage areas;
   a motorized pump for driving a breastpump;
   a pump storage compartment located within said case, sized and shaped to removably receive said motorized pump for driving a breastpump, said pump storage compartment having with at least one pump outlet accessible from said case exterior;
   a cover on said pump storage compartment through which said pump storage compartment and said outlet are accessed;
   at least one adjustable back strap having an upper shoulder engaging portion and a lower bottom portion mounted on the back of said case; and
   said horizontal shelf is collapsible within said backpack.

5. A carrier for a breastpump, comprising:
   a backpack having an interior and an exterior, said backpack having a top, bottom and sides defining exterior walls to the backpack;
   a motorized pump that is operable to drive a breast-engaging device for the expression of milk, said pump generating a cyclical pressure and having an outlet through which said pressure is communicated; and
   a pump compartment formed within said backpack interior and within which said motorized pump is removably mounted, said pump compartment having a cover which is openable from said backpack exterior to access said pump for use thereof without removing said pump from said pump compartment, said pump compartment being collapsible such that said backpack interior is fully usable with said pump removed.

6. The carrier of claim 5 further including a cold-storage insulated compartment within said backpack interior.

7. The carrier of claim 6 wherein said cold-storage insulated compartment is accessible from said exterior.

8. The carrier of claim 5 further including a milk-storage compartment within said backpack interior and wherein said milk storage compartment is accessible from said exterior.

9. The carrier of claim 8 wherein said milk-storage compartment is a container removably received in said interior, and said pump is removably received in said pump compartment, whereby said pump and said milk-storage container are removable from said backpack without any tool.

10. The carrier of claim 9 further including a shelf, said shelf being mounted within said interior and dividing said interior into an upper and a lower part, said shelf being mounted in a manner to be collapsed when said pump and said milk-storage container are removed.

11. The carrier of claim 10 wherein said milk-storage container is received in said upper part and sits upon said shelf.

* * * * *